United States Patent [19]

Schinzel

[11] 4,133,953
[45] Jan. 9, 1979

[54] PROCESS FOR THE PREPARATION OF SULFONATED BENZOFURAN DERIVATIVES

[75] Inventor: Erich Schinzel, Hofheim am Taunus, Fed. Rep. of Germany

[73] Assignee: Hoechst Aktiengesellschaft, Frankfurt am Main, Fed. Rep. of Germany

[21] Appl. No.: 885,349

[22] Filed: Mar. 13, 1978

[30] Foreign Application Priority Data

Mar. 16, 1977 [DE] Fed. Rep. of Germany ....... 2711363

[51] Int. Cl.$^2$ .................. C07D 307/79; C07D 307/82
[52] U.S. Cl. .................................... 542/454; 542/464; 542/466; 260/332.2 A; 260/332.3 H; 260/346.22; 260/346.71
[58] Field of Search ...................... 260/346.22, 346.71, 260/332.2 A, 332.3 H; 542/454, 464, 466

[56] References Cited

U.S. PATENT DOCUMENTS 3,859,350   1/1975   Sahm et al. ..................... 260/346.22

OTHER PUBLICATIONS

Kost et al., J. Org. Chem. USSR, 6(7), 1516–1517 (1970).

Primary Examiner—Henry R. Jiles
Assistant Examiner—Bernard Dentz
Attorney, Agent, or Firm—Connolly and Hutz

[57] ABSTRACT

Process for the preparation of sulfonated bis-[benzofuranyl-(2)] compounds by treating the corresponding unsulfonated bis-[benzofuranyl-(3)] compounds with sulfuric acid having a content of from 90 to 100% and isolating the mono- and polysulfonic acids formed as such or after conversion into their salts.

4 Claims, No Drawings

PROCESS FOR THE PREPARATION OF SULFONATED BENZOFURAN DERIVATIVES

The present invention relates to a process for the preparation of sulfonated benzofuran derivatives.

It has already been proposed to prepare 2-naphthyl-benzofurans by heating α- or β-phenoxyacetyl-naphthalenes in polyphosphoric acid to a temperature in the range of from 135 to 140° C. (I. N. Chatterjea et al., J. Indian Chem. Soc. 47, 261 (1970)).

In an analogous manner the 2-phenyl-benzofuran can be prepared while starting from ω-phenoxy-acetophenone by the action of hydrofluoric acid (O. Dann et al., Chem. Ber. 91, 172 (1958)).

It has now been found that the bis-[benzofuranyl-(2)-] compounds of the general formula (I)

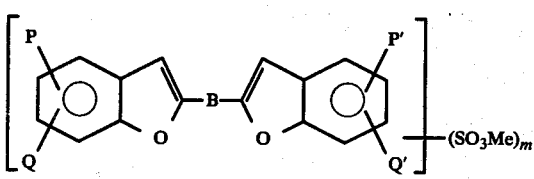

in which B represents a direct bond or one of the groups specified below

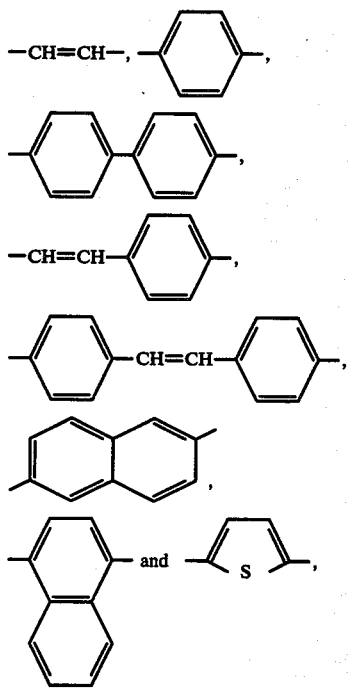

P, Q, P' and Q' represent, independent of each other, hydrogen or halogen atoms, lower alkyl, lower alkoxy or phenyl groups, optionally functionally modified carboxyl groups, or P and Q as well as P' and Q' together stand for a lower alkylene radical or a fused benzene nucleus, Me is hydrogen, an alkali metal or alkaline earth metal cation or an ammonium ion, and m represents the numbers 1, 2, 3 and 4, can be prepared, if sulfuric acid with a content of from 90 to 100% of $H_2SO_4$ is allowed to react with bis-[benzofuranyl-(3)] compounds (II)

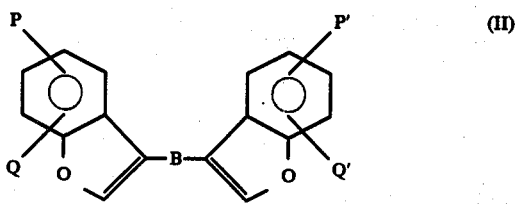

at a temperature of from 0 to 100° C., preferably from 20 to 80° C. over a period of from 3 to 20 hours, and the mono- and/or polysulfonic acids are isolated as such or after conversion into their salts. In the compounds (II) the radicals B, P, P' and Q, Q' are defined as in formula (I) above.

Under the action of sulfuric acid on the bis-benzofuranyl compounds (II) under the conditions specified above, two reaction steps proceed surprisingly one after the other and/or partly simultaneously: first, the introduction of up to 4 sulfonic acid groups and in the second place the rearrangement of the benzofuranyl-(3) into benzofuranyl-(2) radicals.

As the bis-[benzofuranyl-(2)] compounds (I) in aqueous solution are strongly fluorescent, however, the bis-[benzofuranyl-(3)] derivatives (II) in the pure state do not show any fluorescence, the development of the rearrangement within a certain period of time can be observed in a simple manner. Depending on the reaction conditions and the nature of the radicals B, P, P' and Q, Q', there is observed under the action of sulfuric acid on the compounds (II) first the introduction of sulfuric acid groups with the formation of water-soluble bis-benzofuranyl-(3)-sulfonic acids which show partly only a very slight fluorescence and which are converted with increasing temperatures and/or a prolonged reaction time into the bis-[benzofuranyl-(2)]-sulfonic acids showing a strong fluorescence.

The polysulfonates (I) obtained from the compounds (II) by the action of sulfuric acid in the manner described above have been proved by way of the IR-spctroscopic comparison to be practically identical with those polysulfonates which have been obtained by the sulfonation of the bis-[benzofuranyl-(2)] compounds (III) (German Offenlegungsschrift No. 2 238 734).

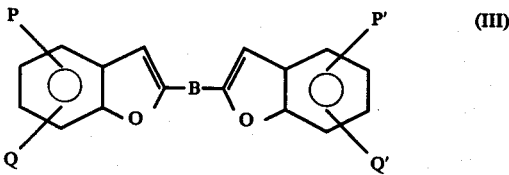

The compounds of the general formula (II) are obtained in known manner by a cyclization with polyphosphoric acid at elevated temperatures of compounds of the general formula (IV)

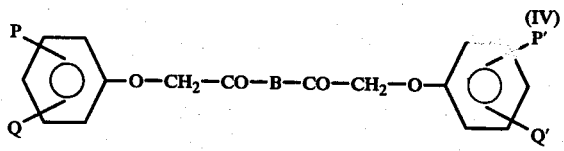

(Ahmed Mustafa, Benzofurans, pages 13 et seq. in the series "The Chemistry of Heterocyclic Compounds" by Weissberger and Taylor). The compounds of the formula (IV) are also obtained according to known processes, for example, by bromination of bis-acetyl compounds of the formula

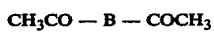

and reaction of the bis-bromoacetyl compounds obtained with the phenol accordingly substituted in the presence of alkali.

By way of the process described above, a technically simple manner has been found to prepare bis-[benzofuranyl-(2)]-sulfonates which represent valuable optical brighteners for several fields of application in the textile and detergent industries.

In the definitions given under P, Q, P' and Q' in the above formulae, there are to be understood by a functionally modified carboxy group first the salts thereof with colorless cations, alkali metal or ammonium ions being preferred, and furthermore those functional derivatives of a carboxy group, in which 3 bonds go from the carbon atoms to hetero atoms, especially the cyano group, a carboxylic acid ester group or a carboxylic acid amide group. By carboxylic acid ester groups there are to be understood especially those of the general formula COOR$^1$, in which R$^1$ represents a phenyl radical or an optionally branched lower alkyl group, these radicals possibly containing further substituents, such as an alkoxy group. By a carboxylic acid amide group there is to be understood especially a group of the formula CONR$^2$R$^3$, in which the radicals R$^2$ and R$^3$ are hydrogen atoms or lower, optionally substituted alkyl groups which may also form a hydroaromatic ring together with the nitrogen atom, furthermore, acid hydrazides and the analogous thio derivatives. By the term "lower" there are to be understood those groups which contain from 1 to 4 carbon atoms.

According to the process of the invention, for example the mono- and polysulfonates of the following bis-[benzofuranyl-(2)] compounds can be obtained:

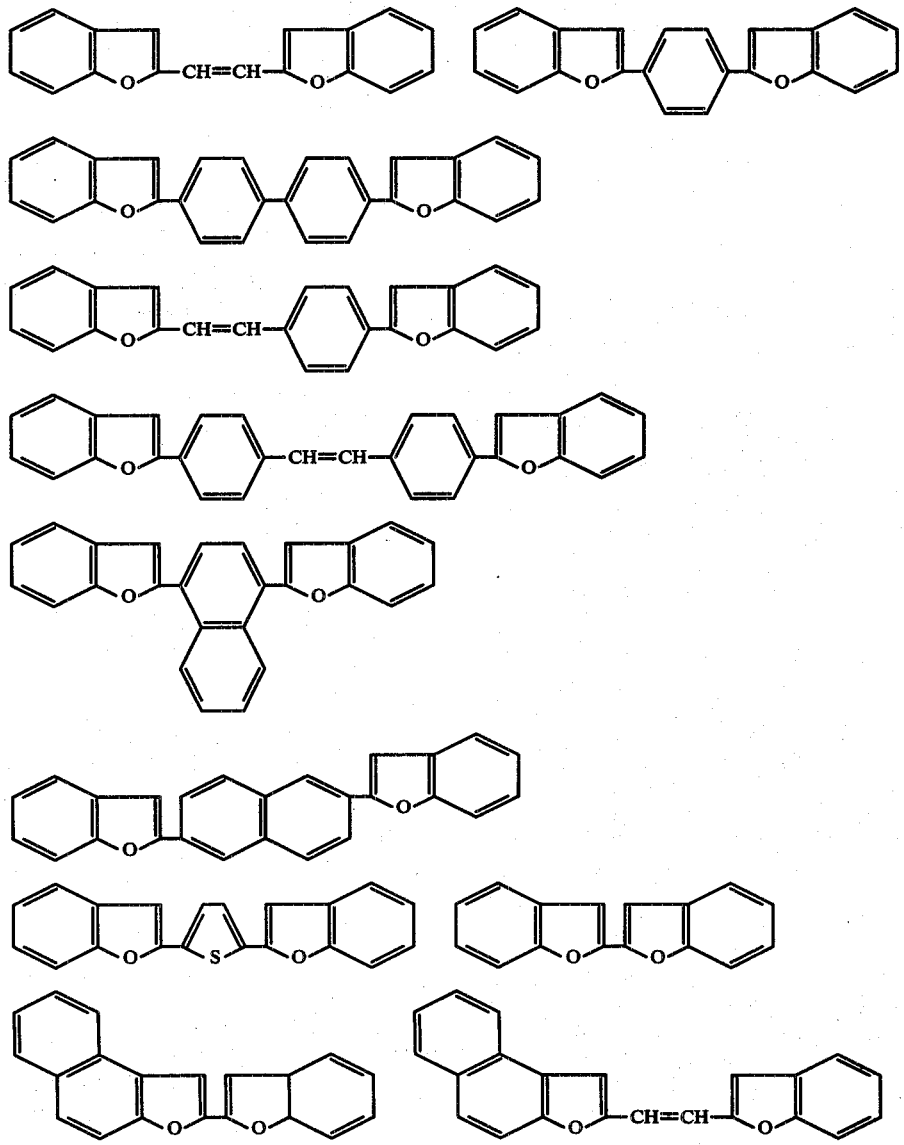

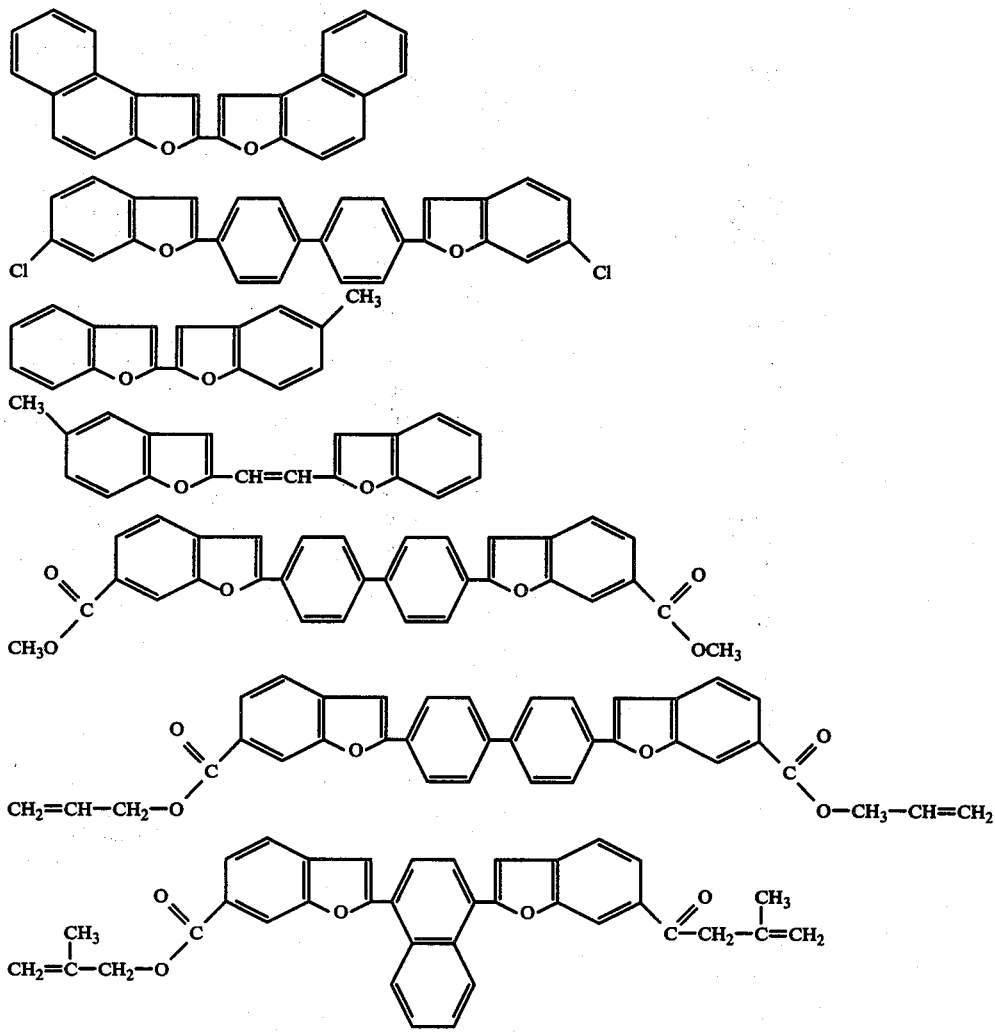

The following Example illustrates the present invention.

EXAMPLE

At a temperature of from 55 to 60° C., 5.8 g of 4,4'-bis-[benzofuranyl-(3)]-diphenyl, melting point 217 to 219° C., are introduced into 186 g of sulfuric acid (of 95 to 97% strength), while stirring and superposing nitrogen, and the mixture is stirred for 12 hours at this temperature. Upon cooling, the mixture is poured onto a mixture of 100 g of ice and 100 ml of water. By neutralization with sodium hydroxide solution and subsequent salting out of the clarified solution with sodium chloride a slightly colored product is obtained, which is dried at 60° C. in vacuo until the weight is constant. 32.3 Grams of a salt mixture are obtained which contains besides sodium chloride and sodium sulfate 10.2 g of the sodium salt of the following tetrasulfonic acid, which corresponds to a yield of 86% of the theory The tetrasulfonate prepared in this manner shows in an aqueous solution a strong reddish-blue fluorescence and — by an IR spectroscopic comparison, as well as when comparing the spectral data and the properties with regard to application — proves to be identical with a tetrasulfonate which was obtained by sulfonation of the 4,4'-bis-[benzofuranyl-(2)]-diphenyl of a melting point of 365 to 370° C.

The 4,4'-bis-[benzofuranyl-(3)]-diphenyl required as starting compound can be prepared in the following manner:

At a temperature of 40° C., 240 g of bromine are added dropwise, while stirring, in the course of 1 hour, to a suspension of 178.5 g of 4,4'-bis-acetyl-diphenyl in 1500 ml of glacial acetic acid, to which a few drops of hydrobromic acid have been added, and the reaction mixture is continued to be stirred for 2.5 hours at this temperature. It is then cooled to room temperature, and the brownish bromination product is isolated on a suc-

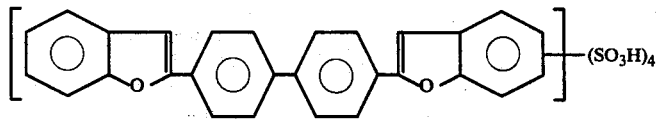

tion-filter. After washing with 750 ml of glacial acetic acid and water, 273 g of the 4,4'-bis-bromoacetyl-diphenyl are obtained, which melts after redissolving from chlorobenzene at a temperature of from 208 to 210° C. under decomposition.

217 Grams of potassium carbonate are introduced, while stirring, into a solution of 147.7 g of phenol in 930 ml of dimethyl formamide. Within about 15 minutes, 208 g of the 4,4'-bis-bromo-acetyl-diphenyl are added portionwise at a temperature of less than 220° C. The mixture is stirred for 5 hours at 15° C. and subsequently for another 15 hours at room temperature. Upon cooling to 5° C., the product is filtered off with suction and is washed with dimethyl formamide and then with water, until it is free from bromine ions. After drying at 60° C. in vacuo, 133 g of the 4,4'-bis-phenoxy-acetyl-diphenyl are obtained which have a melting point of from 176 to 179° C.

At a temperature of from 95 to 100° C., 84.4 g of the 4,4'-bis-phenoxy-acetyl-diphenyl are introduced into 844 g of polyphosphoric acid, while stirring and under an atmosphere of nitrogen. The mixture is stirred for 31 hours at 95 to 100° C., is cooled to 60° C., and 1 liter of water is added dropwise at this temperature. The reaction mixture is then continued to be stirred for 30 minutes, thereafter the product is filtered off with suction at room temperature and is washed with water until neutral. Upon drying in vacuo at 60° C., 76.2 g of the 4,4'-bis-[benzofuranyl-(3)]-diphenyl are obtained as a yellowish powder which after redissolving from toluene shows a melting point in the range of from 217 to 219° C.

The precursors specified in the following Tables 1 and 2 are prepared in an analogous manner:

TABLE 1

R—O—CH₂CO—⟨⟩—⟨⟩—COCH₂—O—R

| No. | R | Melting point | purified from: |
|---|---|---|---|
| 101 | phenyl | 176–179° C | chlorobenzene |
| 102 | 4-methylphenyl | 169–171° C | chlorobenzene |
| 103 | 2-methylphenyl | 161–162° C | chlorobenzene |
| 104 | 2,4-dimethylphenyl | 188–193° C | toluene |
| 105 | 3,4-dimethylphenyl | 166–168° C | chlorobenzene |

TABLE 2

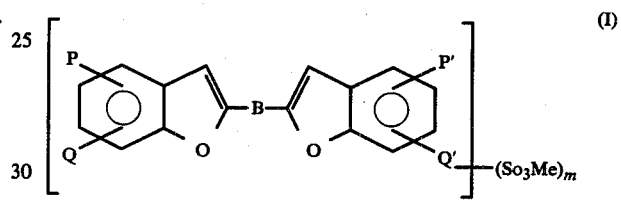

| No. | R₁ | R₂ | Position | Melting point | purified from |
|---|---|---|---|---|---|
| 106 | H, | H | —, — | 217–219° C | toluene |
| 107 | CH₃, | H | 5, — | 241–243° C | chlorobenzene |
| 108 | H, | CH₃ | —, 7 | 221–223° C | chlorobenzene |
| 109 | CH₃, | CH₃ | 4, 6 | 214–216° C | chlorobenzene |
| 110 | CH₃, | CH₃ | 5, 7 | 217–219° C | dimethylformamide |

The sulfonating rearrangement of the benzofuranyl-(3) derivatives specified in Table 2 to give the tetrasulfonates of the corresponding benzofuranyl-(2) compounds melting at very high temperatures and under decomposition only is effected to the method described in Example 1.

What is claimed is:
1. Process for the preparation of bis-[benzofuranyl-(2)] compounds of the general formula (I)

$$\left[ \begin{array}{c} P \\ Q \end{array} \bigcirc \bigcirc \begin{array}{c} \\ O \end{array} B \begin{array}{c} \\ O \end{array} \bigcirc \bigcirc \begin{array}{c} P' \\ Q' \end{array} \right] (SO_3Me)_m \qquad (I)$$

in which
B represents a direct bond or one of the groups specified below

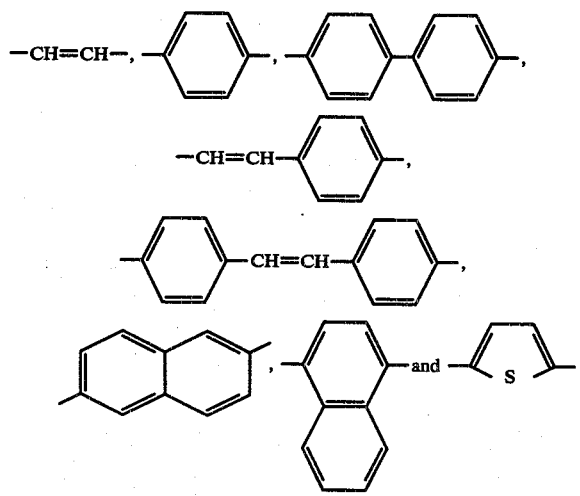

P, Q, P' and Q' represent, independent of each other, hydrogen or halogen atoms, lower alkyl, lower alkoxy or phenyl groups, optionally functionally modified carboxy groups, or P and Q as well as P' and Q' together stand for a lower alkylene radical or a fused benzene nucleus,
Me is hydrogen, an alkali metal or alkaline earth metal cation or an ammonium ion, and
m represents the numbers 1, 2, 3 and 4, which comprises allowing sulfuric acid having a content of from 90 to 100% to act upon bis-[benzofuranyl-(3)] compounds (II)

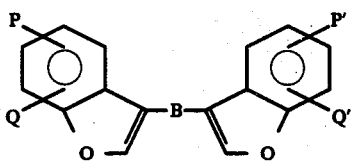 (II)

and isolating the mono- and polysulfonic acids formed as such or after conversion into their salts.

2. Process as claimed in claim 1, wherein a compound of formula I is prepared wherein P, Q, P' and Q' are hydrogen, lower alkyl, lower alkoxy, chlorine or phenyl, B is P,P'-diphenylene, p-phenylene or 2,6-naphthylene and m and Me are as defined in claim 1.

3. Process as claimed in claim 1, which comprises effecting the action of sulfuric acid at a temperature in the range of from 0 to 100° C., preferably from 20 to 80° C.

4. Process as claimed in claim 1, which comprises allowing the sulfuric acid to act upon the compounds of the formula (II) for 3 to 20 hours.

* * * * *